United States Patent [19]

Crivello

[11] 4,417,061

[45] Nov. 22, 1983

[54] PHOTOINITIATORS

[75] Inventor: James V. Crivello, Clifton Park, N.Y.

[73] Assignee: General Electric Company, Schenectady, N.Y.

[21] Appl. No.: 320,996

[22] Filed: Nov. 13, 1981

Related U.S. Application Data

[60] Division of Ser. No. 150,974, May 19, 1980, abandoned, which is a continuation of Ser. No. 13,116, Feb. 21, 1979, abandoned, which is a continuation of Ser. No. 833,146, Sep. 14, 1977, Pat. No. 4,161,478, which is a continuation-in-part of Ser. No. 789,419, Apr. 21, 1977, Pat. No. 4,136,102, which is a division of Ser. No. 574,006, May 2, 1975, abandoned, which is a continuation-in-part of Ser. No. 466,374, May 2, 1974, abandoned, Ser. No. 466,375, May 2, 1974, abandoned, and Ser. No. 466,378, May 2, 1974, abandoned.

[51] Int. Cl.$^3$ .............................................. C07F 9/80
[52] U.S. Cl. ............................................................ 549/3
[58] Field of Search ................................................. 549/3

[56] References Cited

U.S. PATENT DOCUMENTS

| | | | |
|---|---|---|---|
| 4,116,886 | 9/1978 | Cella | 260/440 X |
| 4,161,478 | 7/1979 | Crivello | 260/440 X |
| 4,219,654 | 8/1980 | Crivello | 260/440 X |

Primary Examiner—Helen M. S. Sneed
Attorney, Agent, or Firm—William A. Teoli; James C. Davis, Jr.; James Magee, Jr.

[57] ABSTRACT

Onium salts of Group IVa elements having an $MF_6^-$ anion, where M is selected from P, As and Sb, have been found to be photo active under ultraviolet light. These onium salts can be employed as cationic photoinitiators when used with a variety of organic resins and cyclic organic compounds.

11 Claims, No Drawings

PHOTOINITIATORS

This application is a division of application Ser. No. 150,974, filed May 19, 1980, now abandoned, which is a continuation of application Ser. No. 13,166, filed Feb. 21, 1979, now abandoned, which is a continuation of 833,146, filled Sept. 14, 1977, now U.S. Pat. No. 4,161,478, which is a continuation-in-part of my copending application Ser. No. 789,419, filed Apr. 21, 1977, now U.S. Pat. No. 4,136,102, which is a division of copending application Ser. No. 574,006, filed May 2, 1975, now abandoned, which is a continuation-in-part of applications Ser. Nos. 466,374, 466,375 and 466,378, filed concurrently on May 2, 1974, now abandoned, where all of the aforesaid applications are assigned to the same assignee as the present invention. The present invention relates to onium salt photoinitiators of Group VIa elements having an $MF_6$ anion, where M is an element selected from P, As and Sb.

The photoinitiator compositions of the present invention can be used in combination with various photopolymerizable organic materials, such as cyclic ethers, cyclic esters, polyvinyl acetals, eposy resins, etc., to produce UV curable compositions and heat curable compositions. The photoinitiators of the present invention are included by the formula, $$[(R)_a (R^1)_b (R^2)_c X] [MF_6], \quad (1)$$

where R is a monovalent aromatic organic radical, $R^1$ is a monovalent organic aliphatic radical, selected from alkyl, cycloalkyl and derivatives thereof, $R^2$ is a polyvalent organic radical forming a heterocyclic or fused ring structure, selected from aliphatic radicals and aromatic radicals, X is a Group VIa element selected from sulfur and selenium, M is selected from P, As and Sb, a is a whole number equal to 0 to 3 inclusive, b is a whole number equal to 0 to 2 inclusive, c is a whole number equal to 0 or 1 and the sum of $a+b+c$ is a value equal to 3 or the valence of X Radicals included by R can be the same or different aromatic carbocyclic or heterocyclic radicals having from 4-20 carbon atoms which can be substituted with from 1 to 4 monovalent radicals selected from $C_{(1-8)}$ alkoxy, $C_{(1-8)}$ alkyl, nitro, chloro, etc. R is more particularly phenyl, chloro phenyl, nitro phenyl, methoxy phenyl, pyridyl, etc. $R^1$ radicals include $C_{(1-8)}$ alkyl, such as methyl, ethyl, etc., substituted alkyls, such as $-C_2H_4OCH_3$, $-CH_2COOC_2H_5$, $-CH_2COCH_3$, etc. $R^2$ radicals include such structures as

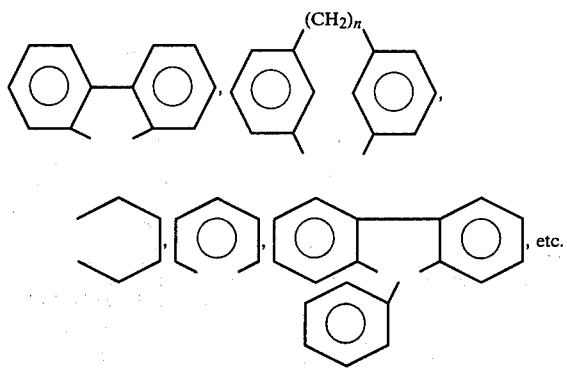

Group VIa onium salts included by formula (1) are, for example,

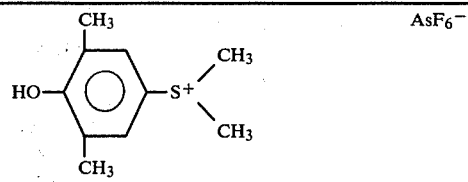

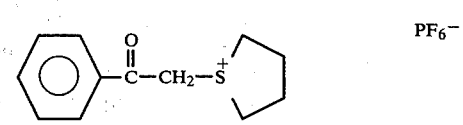

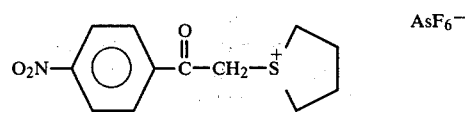

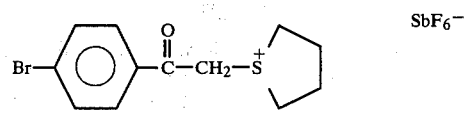

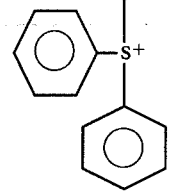

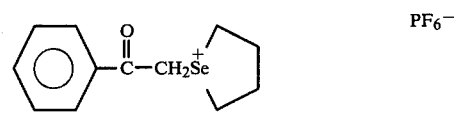

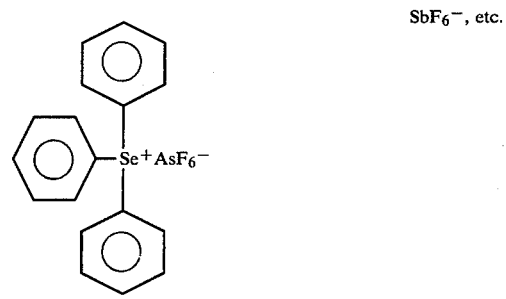

The Group VIa onium salts of formula (1) can be made by procedures shown in the copending application Ser. No. 833,279 filed 9/14/77, now abandoned of James V. Crivello and Julia H. W. Lam, filed concurrently herewith and assigned to the same assignee as the present invention. An aryl iodonium salt such as diphenyliodonium hexafluoroarsenate is employed with a Group VIa compound, such as diphenylsulfide in the presence of a copper salt catalyst, for example, copper benzoate at temperatures in the range of from 50° C. to 250° C. for one to five hours. Other procedures which can be used are shown in J. W. Knapczyk and W. E. McEwen, J. Am. Chem. Soc., 91 (1969): A. L. Maycock and G. A. Berchtold, J. Org. Chem., 35 No. 8, 2532 (1970); H. M. Pitt U.S. Pat. No. 2,807,648, E. Goethals and P. De Radzetzky, Bul. Soc. Chim. Belg., 73 546 (1964); H. M. Leichester and F. W. Bergstrom, J. Am. Chem. Soc., 51 3587 (1929), etc.

The Group VIa onium salts of formula (1) can be employed as photoinitiators for effecting the cure of a variety of cationically polymerizable organic materials such as epoxy resins, cyclic ethers, polyvinyl acetals, which are described previously in my copending application Ser. No. 768,074, filed Feb. 14, 1977 now Pat. No. 4,102,687, for curing phenol-formaldehyde resins and in my copending application Ser. No. 732,421, filed Oct. 14, 1976 now abandoned, directed to the use of compounds of formula (1) for curing polyvinyl acetal resins.

In order that those skilled in the art will be better able to practice the present invention, the following examples are given by way of illustration and not by way of limitation. All parts are by weight.

EXAMPLE 1

Triphenylselenonium chloride was prepared according to the procedure of H. M. Leichester and F. W. Bergstrom, J. Am. Chem. Soc., 51 3587 (1929) starting with diphenyl selenide. The corresponding fluoroborate, hexafluoroarsenate and hexafluoroantimonate salts were prepared by ading sodium hexafluoroarsenate, sodium tetrafluoroborate or potassium hexafluoroantimonate to an aqueous solution of triphenylselenonium chloride. White crystalline solids were obtained which were dried in vacuo.

Three percent solutions of the above salts in 4-vinylcyclohexene dioxide were cured as 2 mil films at a distance of 6 inches from a GE H3T7 lamp. The following cure times were observed:

| Salt | Cure Time |
|---|---|
| $(C_6H_5)_3Se^+BF_4^-$ | 10 sec. |
| $(C_6H_5)_3Se^+AsF_6^-$ | 5 sec. |
| $(C_6H_5)_3Se^+SbF_6^-$ | 3 sec. |

The above results show that the hexafluoro salt is a superior photosensitizer with respect to cure time as compared to the tetrafluoroborate salt.

EXAMPLE 2

Several sulfonium hexafluoroarsenate salts, sulfonium hexafluoroantimonate salts and selenium hexafluoroarsenate salts, were prepared by adding the corresponding anion in the form of the acid or salt, such as sodium hexafluoroarsenate to the corresponding cation structure, such as an aqueous solution of tri(3,5-dimethyl-4-hydroxy)phenyl sulfonium chloride. The procedure described by H. M. Leichester and F. W. Bergstrom, J. Am. Chem. Soc. 51 3587 (1929) was employed. The following table shows the results obtained.

SULFONIUM SALTS

| Cation Structure | Anion | M.P. (°C.) | λMax (ε Max) | Elemental Analysis | | | |
|---|---|---|---|---|---|---|---|
| | | | | | C | H | S |
| (3,5-dimethyl-4-hydroxyphenyl)dimethylsulfonium | $AsF_6^-$ | 154–156 | 300(3,000) 284(4,100) 279(4,600) 252(9,300) | calc found | 33.20 32.99 | 4.15 3.90 | 8.75 8.92 |
| tri(3,5-dimethyl-4-hydroxyphenyl)sulfonium | $AsF_6^-$ | 245–251 | 263(23,300) 280(20,708) 317(7,150) | calc found | 49.3 49.39 | 4.62 4.59 | 5.48 5.55 |
| | | | | | C | H | Se |
| triphenylselenonium | $AsF_6^-$ | 184–187 | 258(10,900) 266(2,841) 275(2,145) | calc found | 43.3 43.4 | 3.01 2.99 | 15.8 16.0 |
| | | | | | C | H | |
| triphenylselenonium | $SbF_6^-$ | 140–143 | 258(10,900) 266(2,841) 275(2,145) | calc found | 39.6 39.9 | 2.75 2.98 | |
| phenacyltetrahydrothiophenium | $PF_6^-$ | 117–120 | 300(4,700) 248(10,200) | | | | |
| " | $AsF_6^-$ | 161–163 | 300(4,700) | | | | |

| | SULFONIUM SALTS | | | |
|---|---|---|---|---|
| Cation Structure | Anion | M.P. (°C.) | λMax (ε Max) | Elemental Analysis |
| " | SbF$_6^-$ | 160–163 | 248(10,200) 300(4,700) 248(10,200) | |

It was found that 4-vinylcyclohexene dioxide compositions containing the above onium salts exhibited a faster rate of cure, as compared to comparable prior art tetrafluoroborate onium salts.

EXAMPLE 3

A mixture of 11.75 parts of diphenyliodonium hexafluoroarsenate, 4.065 parts of diphenyl sulfide and 0.2 part of copper benzoate was heated with stirring at a temperature of 120°–125° C. for 3 hours. The mixture was then poured while it was hot into a container whereupon the product crystallized. The product was extracted three times with diethylether and then air dried. There was obtained a 97% yield of triphenylsulfonium hexafluoroarsenate. The triphenylsulfonium hexafluoroarsenate product had a melting point of 195°–197° C. after it was further recrystallized from 95% ethanol.

A mixture of 0.02 mole solution of the triphenylsulfonium hexafluoroarsenate in styrene oxide was irradiated at 25° C. in a glass vial sealed under nitrogen using a 450 watt Hanovia lamp. It was found that the styrene oxide polymerized after 5 minutes. The same procedure was repeated, except that there was used tetrahydrofuran.

EXAMPLE 4

The procedure of Example 3 was repeated, except that there was used 12.75 parts of diphenyliodonium hexafluoroarsenate, 2.55 parts of pentamethylene sulfide and 0.2 part of copper benzoate. A 60% yield of product, namely, phenyl penta methylenesulfonium hexafluoroarsenate was obtained after the product was recrystallized from methanol.

EXAMPLE 5

A mixture of 12.75 part of 4,4'-diisopropylphenyliodonium hexafluoroarsenate, 5 parts of phenoxanthene and 0.2 part of copper benzoate was heated under nitrogen with stirring at 120°–125° C. for 3 hours. After cooling the product was extracted with diethylether. The remaining oil was dissolved in methylene chloride and passed through a six inch column of alumina. Trituration with ether followed by cooling in an ice bath gave a white product amounting to a 41% yield of 4-isopropylphenylphenoxanthylium hexafluoroarsenate (m.p.126°–217° C.) having the formula,

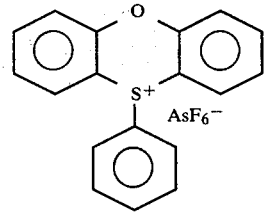

| Analysis | | | |
|---|---|---|---|
| calc | 49.61 | 3.74 | 6.30 |
| found | 49.57 | 3.82 | 6.25 |

A 3% solution of the above onium salt in 3,4-epoxycyclohexylmethyl-3',4'-epoxycyclohexane carboxylate was irradiated with a G. E. H3T7 lamp at a distance of 10 inches. A hard tack-free film was obtained in 30 seconds.

EXAMPLE 6

Following the procedure of Examples 3 and 5, additional Group VIa onium salts of formula (1) were prepared as shown in Table I as follows:

TABLE I

| I$^+$ Salt | Group VIa Compound | VIa Salt | Yield (%) | M.P. (°C.) | Analysis | | | |
|---|---|---|---|---|---|---|---|---|
| | | | | | | % C | % H | % S |
| [Ph]$_2$–I$^+$AsF$_6^-$ | [Ph]$_2$–S | [Ph]$_3$S$^+$AsF$_6^-$ | 97 | 195–197 | calc<br>fnd | 47.7<br>47.78 | 3.3<br>3.41 | 7.06<br>7.06 |
| [i-Pr–Ph]$_2$–I$^+$PF$_6^-$ | [Ph]$_2$–S | i-Pr–Ph–S$^+$–[Ph]$_2$ PF$_6^-$ | 92 | 133–136 | calc<br>fnd | 56.90<br>57.05 | 4.06<br>5.03 | 6.90<br>7.09 |
| [iPr–Ph]$_2$–I$^+$AsF$_6^-$ | [Ph]$_2$–S | iPr–Ph–S$^+$–[Ph]$_2$ AsF$_6^-$ | 88 | 151–152 | calc<br>fnd | 51.01<br>51.05 | 4.25<br>4.34 | 6.48<br>6.44 |
| [CH$_3$–Ph]$_2$–I$^+$AsF$_6^-$ | [Ph]$_2$–S | CH$_3$–Ph–S$^+$–[Ph]$_2$ PF$_6^-$ | 87 | 120–125 | calc<br>fnd | 54.0<br>54.2 | 4.0<br>4.1 | 7.6<br>7.7 |
| [CH$_3$–Ph]$_2$–I$^+$AsF$_6^-$ | [Ph]$_2$–S | C$_2$H$_4$–Ph–S$^+$–[Ph]$_2$ AsF$_6^-$ | 100 | 120–125 | calc<br>fnd | 50.0<br>49.8 | 3.9<br>3.9 | 6.7<br>6.7 |

TABLE I-continued

| I+ Salt | Group VIa Compound | VIa Salt | Yield (%) | M.P. (°C.) | Analysis % C | % H | % S |
|---|---|---|---|---|---|---|---|
| [–⟨⟩–]₂I⁺AsF₆⁻ | [⟨⟩]₂S | –⟨⟩–S⁺–[⟨⟩]₂ AsF₆⁻ | 89 | 143–145 | calc 51.0  fnd 51.2 | 4.0  4.1 | 6.8  6.8 |
| [⟨⟩]₂I⁺AsF₆⁻ | (thianthrene structure) | (thianthrenyl sulfonium AsF₆⁻) | 79 | 165–168 | calc 46.3  fnd 46.2 | 2.8  2.8 | 6.9  7.0 |
| [iPr–⟨⟩–]₂I⁺AsF₆⁻ | (thianthrene structure) | (isopropylphenyl thianthrenyl sulfonium AsF₆⁻) | 41 | 126–127 | calc 49.1  fnd 49.51 | 3.74  3.82 | 6.30  6.25 |
| [CH₃–⟨⟩–]₂I⁺AsF₆⁻ | (thioxanthene-type structure) | (tolyl sulfonium AsF₆⁻) | 95 | 165–167 | calc 50.2  fnd 50.25 | 3.6  3.6 | 6.7  6.67 |
| [Cl–⟨⟩–]₂I⁺AsF₆⁻ | (thianthrene structure) | (chlorophenyl sulfonium AsF₆⁻) | 99 | 183–187 | calc 43.2  fnd 43.1 | 2.4  2.5 | 6.4  6.3 |
| [tBu–⟨⟩–]₂I⁺AsF₆⁻ | (thioxanthene-type structure) | (t-butylphenyl sulfonium AsF₆⁻) | 67 | 182–185 | calc 53.1  fnd 53.0 | 4.4  4.6 | 6.2  6.1 |

EXAMPLE 7

In addition to the Group VIa onium salts of Example 6, additional Group VIa salts were prepared following the procedure of Examples 3 and 5 as shown in Table II as follows:

TABLE II

| I+ Salt | Group VIa Compound | VIa Salt | Yield (%) | M.P. (°C.) | Analysis | | |
|---|---|---|---|---|---|---|---|
| | | | | | | % C | % H | % S |
| (C₆H₅)₂I⁺AsF₆⁻ | tetrahydrothiopyran | (C₆H₅)(tetrahydrothiopyranyl)S⁺ AsF₆⁻ | 60 | 150–151 | calc<br>fnd | 35.87<br>35.69 | 4.08<br>3.98 | 8.70<br>8.63 |
| (C₆H₅)₂I⁺AsF₆⁻ | 1,4-oxathiane | (C₆H₅)(oxathianyl)S⁺ AsF₆⁻ | 67 | 151–153 | calc<br>fnd | 32.43<br>32.33 | 3.51<br>3.53 | 8.65<br>8.37 |
| (i-Pr-C₆H₄)₂I⁺AsF₆⁻ | tetrahydrothiopyran | (i-Pr-C₆H₄)(tetrahydrothiopyranyl)S⁺ AsF₆⁻ | 56 | 120–125 | calc<br>fnd | 40.9<br>40.9 | 5.1<br>5.1 | 7.8<br>7.8 |
| (C₆H₅)₂I⁺AsF₆⁻ | tetrahydrothiophene | (C₆H₅)(tetrahydrothiophenyl)S⁺ AsF₆⁻ | 95 | 110–115 | calc<br>fnd | 33.9<br>33.8 | 3.7<br>3.9 | 9.0<br>9.2 |
| (C₆H₅)₂I⁺AsF₆⁻ | C₆H₅—S—CH₃ | (C₆H₅)₂—S⁺—CH₃ AsF₆⁻ | 97 | 100–102 | calc<br>fnd | 40.0<br>38.53 | 3.33<br>3.39 | 8.21<br>8.53 |

EXAMPLE 8

In accordance with a further aspect of copending application Ser. No. 833,279, a variety of triaryl Group VIa onium salts were prepared using a diaryliodonium hexafluoroarsenate, hexafluoroantimonate or hexafluorophosphate salt and a thiophenol coreactant in combination with copper benzoate and triethylamine as a cocatalyst. The diphenyliodonium hexafluoroarsenate was prepared by the procedure shown in Crivello U.S. Pat. No. 3,981,897, assigned to the same assignee as the present invention. Other procedures which can be used are, for example, M. C. Casserio et al, J. Am. Soc., 81 366 (1959). A typical procedure used in preparing such triaryl Group VIa onium salts was as follows:

A mixture of 2.75 part of thiophenol, 11.75 parts of diphenyliodonium hexafluoroarsenate, 0.2 part of copper benzoate and 4 parts of tri-n-butyl amine were heated with stirring at 120°–125° C. under nitrogen for 3 hours. The product after cooling was washed with diethylether and then dried. There was obtained an 86% yield of triphenylsulfonium hexafluoroarsenate. Additional triaryl Group VIa onium salts were prepared as follows following substantially the same procedure:

TABLE III

| I+ Salt | Group VIa Compound | VIa Salt | Yield (%) | M.P. (°C.) |
|---|---|---|---|---|
| (CH₃—C₆H₄)₂I⁺AsF₆⁻ | CH₃—C₆H₄—SH | (CH₃—C₆H₄)₃S⁺AsF₆⁻ | 98 | 164–167 |

TABLE III-continued

| I+ Salt | Group VIa Compound | VIa Salt | Yield (%) | M.P. (°C.) |
|---|---|---|---|---|
| (C₆H₅)₂I+AsF₆⁻ | Cl–C₆H₄–SH | (C₆H₅)₂S+–C₆H₄–Cl AsF₆⁻ | 12.1 | 123–127 |
| (C₆H₅)₂I+AsF₆⁻ | F–C₆H₄–SH | (C₆H₅)₂S+–C₆H₄–F AsF₆⁻ | 17 | 140/14 143 |
| [C₆H₅]₂I+AsF₆⁻ | C₆H₅–SH | [C₆H₅]₃S+AsF₆⁻ | 89 | 194–197 |

Although the above examples are directed to only a few of the very many compounds included within the scope of formula (1), a further definition of the Group VIa onium salts are as follows:

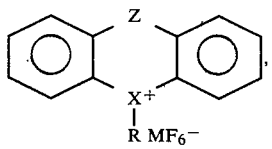

where M, X and R are as previously defined, and Z is a member selected from the class consisting of —S—, $$-\overset{O}{\underset{}{S}}-,\ -\overset{O}{\underset{O}{S}}-,\ -\overset{O}{\underset{}{C}}-,$$

O, Se, CH₂, C₂H₄, and $$-\overset{R^4}{\underset{}{N}}-,$$

and R⁴ is selected from C$_{(1-8)}$ alkyl and C$_{(6-13)}$ aryl.

What I claim as new and desire to secure by Letters Patent of the United States is:

1. A sulfonium or selenium salt having an MF₆ anion, where M is selected from the class consisting of phosphorus, arsenic and antimony, where the valence of the sulfonium or selenium salt cation is satisfied by a C$_{(6-12)}$ arylacyl radical and a divalent aliphatic radical.

2. A sulfonium or selenium salt having an MF₆ anion, where M is selected from the class consisting of phosphorus, arsenic and antimony, where the valence of the sulfonium or selenium salt cation is satisfied by a hydroxyphenyl radical or a substituted hydroxyphenyl radical and a divalent aliphatic radical.

3. A compound in accordance with claim 2 having the formula,

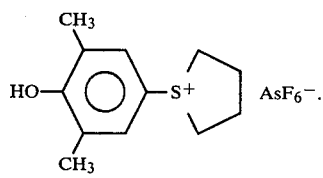

4. A compound in accordance with claim 2 having the formula,

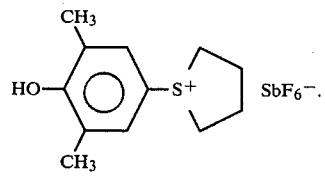

5. A compound in accordance with claim 2 having the formula,

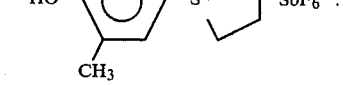

6. A sulfonium salt in accordance with claim 1 having the formula,

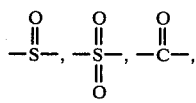

7. A sulfoniam salt in accordance with claim 1 having the formula,

8. A sulfonium salt in accordance with claim 1 having the formula,

9. A sulfonium salt in accordance with claim 1 having the formula,

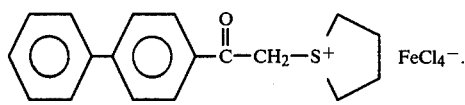
10. A sulfonium salt in accordance with claim 1 having the formula,
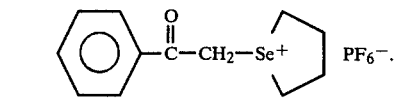
11. A selenium salt in accordance with claim 1 having the formula,
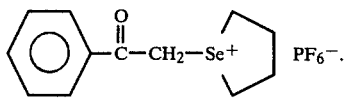
* * * * *